United States Patent [19]

Wood

[11] 4,434,651
[45] Mar. 6, 1984

[54] HARDNESS TEST INDENTERS

[75] Inventor: Jill E. G. Wood, Hampton, England

[73] Assignee: The Secretary of State for Industry in Her Britannic Majesty's government of the United Kingdom of Great Britain and Northern Ireland, London, England

[21] Appl. No.: 372,608

[22] Filed: Apr. 28, 1982

[30] Foreign Application Priority Data

May 6, 1981 [GB] United Kingdom ................. 8113740

[51] Int. Cl.³ ............................................. G01N 3/40
[52] U.S. Cl. ...................................................... 73/85
[58] Field of Search ................... 73/78, 79, 81, 82, 83, 73/85

[56] References Cited

U.S. PATENT DOCUMENTS 2,091,995  9/1937  Knoop .

Primary Examiner—S. Clement Swisher
Attorney, Agent, or Firm—Pollock, VandeSande & Priddy

[57] ABSTRACT

A hardness test indenter having a retangular base and four operative plane faces, a first pair of said faces meeting each other in a straight ridge with an included angle in the range from about 60° to about 150°; and a second pair of said faces making substantially equal angles with said straight ridge and so disposed in relation to one another and to said ridge that the first pair of faces have edges substantially symmetrically disposed in relation to said straight ridge; and said second pair of faces having between them an included angle in the range from about 60° to about 150°; the said straight ridge having a length not more than about 0.5 millimeter and not less than about 0.05 millimeter.

5 Claims, 3 Drawing Figures

HARDNESS TEST INDENTERS

This invention relates to hardness test indenters, more especially usable in the kind of hardness test in which a preliminary load and an additional load are used to drive an indenter into a specimen under test, and where a measurement of the depth of penetration is made.

It has been usual to use for an indenter for such tests, more especially on harder materials, a diamond cone with a spherically radiused tip, and on such an indenter have been based widely recognized scales of hardness, eg the Rockwell scales. However, a diamond cone indenter cannot be made to specified shape with perfect accuracy, and it is also expensive and time consuming to recondition such an indenter to its original shape and surface finish.

The present invention provides an indenter having a form which can be accurately reproduced and which is appreciably cheaper to manufacture and to maintain than the conventional conical indenter.

According to the invention, a hardness test indenter has a rectangular base and four operative plane faces, a first pair of said faces meeting each other in a straight ridge with an included angle in the range from about 60° to about 150°; and a second pair of said faces making substantially equal angles with said straight ridge and so disposed in relation to one another and to said ridge that the first pair of faces have edges substantially symmetrically disposed in relation to said straight ridge; and said second pair of faces having between them an included angle in the range from about 60° to about 150°; the said straight ridge having an appreciable length, not more than about 0.5 millimeter, and more than about 0.05 millimeter.

In one embodiment of the invention the included angle between said first pair of faces and between said second pair of faces is 111°±0.1°, and preferably the length of said straight ridge is 0.255±0.005 millimeter.

A preferred material in which the indenter is made is diamond.

The invention will be further described, by way of example only, with reference to the accompanying drawing in which FIG. 1 is an elevation of an indenter according to the invention.

Figure 1:
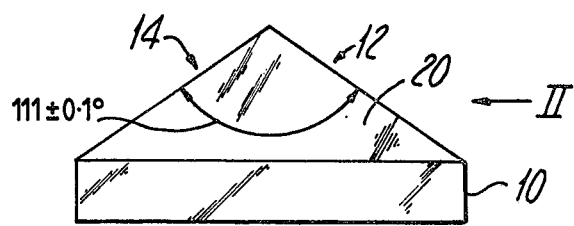
Figure 2:
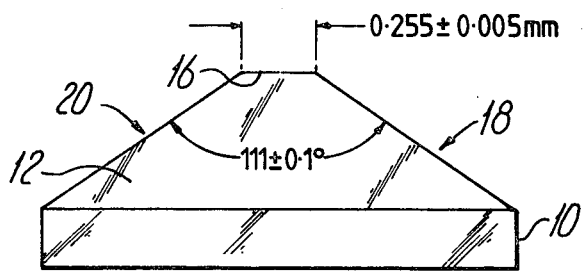
FIG. 2 is an elevation in the direction of the arrow II in FIG. 1.
Figure 3:
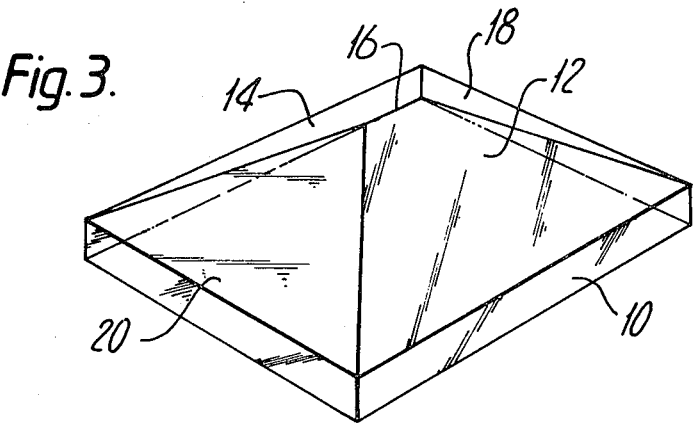
FIG. 3 is a perspective view of the indenter.

A hardness test indenter, in one embodiment, has a base 10 of rectangular plan. To facilitate mounting and to limit the risk of chipping, the base is made, at least approximately, in the shape of a four-sided prism. The indenter has four operative plane faces. A first pair of said operative faces are referenced 12 and 14. The faces 12 and 14 meet in a ridge 16, so that faces 12 and 14 are trapezium shaped. The second pair of operative faces are referenced 18 and 20. These faces are triangular and in each face the apex remote from the base 10 coincides with an end of the ridge 16. In this embodiment the angle included between the first pair of faces 12 and 14 is 111±0.1 and the same angle is included between the second pair of faces 18 and 20, while the length of the ridge 16 is 0.255±0.005 millimeter. All the operative faces are symmetrically arranged in relation to an axis normal to the base of the indenter, and passing through the center thereof. The indenter is made from diamond and the ridge 16 is not ground to a specific radius, but approximates in form to the intersection between two geometric planes.

It is found that the indenter, in the embodiment just described, produces hardness test results which compare very closely with conventional values for the same material according to the Rockwell C scale (RTM); making indentations, both under preliminary and total applied loads, which are closely similar in depth to those made by the standard conical indenter. By varying the included angle between operative faces of the indenter, and also the length of the ridge 16, close approximations to other Rockwell hardness scales can, if desired, be achieved.

The conventional diamond cone indenter is not ideal in that diamond as a substance does not naturally conform to a circular or spherical shape. This leads to problems in manufacture. Other forms of indenter are, of course, possible, including a truncated cone, and pointed and truncated pyramids. It has been found that a pointed pyramid makes indentations which are too deep to provide really good comparison with the established scales; moreover, a pointed pyramid is not easy to form precisely. A truncated indenter, although reasonably easy to make, tends to have an opposite effect, and too small a penetration takes place under preliminary load. Further background information, theory and comparative experimental results may be obtained from National Physical Laboratory Report MOM 41, 1981.

In the particular embodiment described above, an indenter according to the invention is made of diamond, but alternatively could be fabricated of another very hard material, for example a hard form of boron nitride.

I claim:

1. A hardness test indenter shaped as a pyramid having a rectangular base whose diagonals are of equal length, said pyramid shaped indenter having four operative plane faces which respectively extend toward one another from the four sides of said rectangular base and which meet one another at five edges, a first pair of said faces being trapezium shaped and extending toward one another from two opposite sides of said rectangular base, said first pair of faces meeting each other in a straight ridge with an included angle in the range from about 60° to about 150°, said straight ridge being one of said five edges and being located in spaced relation to and mid-way between said two opposite sides of said rectangular base; and a second pair of said faces extending toward one another from the other two opposite sides of said rectangular base and making substantially equal angles with said straight ridge, said second pair of faces being triangular in shape and having apices which are coincident with the opposing ends of said straight ridge respectively, the sides of said triangular second faces leading to said apices meeting the sides of said trapezium shaped first pair of faces leading to the opposing ends of said straight ridge to provide the other four of said edges, said other four edges being symmetrically disposed in relation to said straight ridge and all of said four edges being equal in length to one another; and said second pair of faces having between them an included angle in the range from about 60° to about 150°; the said straight ridge having a length not more than about 0.5 millimeter and not less than about 0.05 millimeter.

2. A hardness test indenter according to claim 1 wherein the length of said straight ridge is 0.255±0.005 millimeter.

3. A hardness test indenter according to claim 1 which is made of diamond.

4. A hardness test indenter according to claim 1 which is made of a hard form of boron nitride.

5. A hardness test indenter having a rectangular base and four operative plane faces, a first pair of said faces meeting each other in a straight ridge; and a second pair of said faces making substantially equal angles with said straight ridge and so disposed in relation to one another and to said ridge that the first pair of faces have edges substantially symmetrically disposed in relation to said straight ridge; the included angle between said first pair of faces and between said second pair of faces being 111°±0.1°; and the said straight ridge having a length not more than about 0.5 millimeter and not less than about 0.05 millimeter.

* * * * *